United States Patent [19]

Holtkamp, Sr.

[11] Plant 4,154

[45] Nov. 22, 1977

[54] AFRICAN VIOLET PLANT

[76] Inventor: Hermann Holtkamp, Sr., Kueningsmuehle, 2-Dingden, 4236 Hamminkeln, Germany

[21] Appl. No.: 730,356

[22] Filed: Oct. 7, 1976

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

This invention relates to a novel African Violet plant having violet-blue blossoms of large size, borne over a long period on strong, upright stems.

1 Drawing Figure

1

The present invention comprises a new and distinct cultivar of African Violet plant, botanically known as *Saintpaulia ionantha,* and hereinafter referred to by the cultivar name Evelyn. Evelyn, which was identified during the seedling selection process by No. 17/75 blue, is a product of a planned breeding program which had the objective of creating a new African Violet cultivar with violet-blue flower color, strong upright stems, fast and vigorous growth, profuse flowering, uniform bouquet, and prolonged blooming period. These traits in combination were not present in previously available commercial cultivars.

The new cultivar was originated from a cross made in a controlled breeding program in Isselburg, Rhineland, Germany. The female, or seed parent was an unpatented cultivar known as Type XIX 4295. The male, or pollen parent was an unpatented cultivar identified as Type XIX 4231.

The new cultivar Evelyn was discovered and selected as a flowering plant within the progeny of the stated cross by me in a controlled environment in Isselburg, Rhineland, Germany.

Asexual reproduction of the new cultivar by leaf cutting and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Evelyn, which in combination distinguish this African Violet as a new and distinct cultivar:

1. Relatively large flower size.
2. Violet-blue flower color.
3. Foliage color.
4. Fast and vigorous growth, and
5. Profuse flowering on strong stems, and long blooming period.

The accompanying photographic drawing shows a typical specimen plant of the new cultivar. The colors appearing in the photograph are as true as possible with color illustrations of this type.

In the following description, color references are made to the Horticultural color chart issued by Wilson Colour Ltd., except where general color terms of ordinary significance are obvious.

2

Botanical classification: *Saintpaulia ionantha,* Ramat. cv. Evelyn.

Parentage:

*Male parent.*—Cultivar XIX 4231, a moorish blue African Violet, color value 739/2.

*Female parent.*—Cultivar XIX 4295, victoria violet in color, No. 738/2.

Propagation: The new cultivar holds its distinguishing characteristics through successive propagations by leaf cuttings and by division of shoots.

Plant: From 8 cm. to 10 cm. tall when grown in pots, and approximately 35 cm. in diameter when fully grown.

*Leaves.*—General form: round to oval. Diameter: 6–7.5 cm. Texture: soft. Aspect: shiny and slightly hairy. Veins: underside strong, pronounced reddish-green. Color (upperside): spinach green 0960. Color (underside): light green 60/3. Petiole: brown-red to green.

Flowers:

*Buds.*—Cup-shaped, 1–3 mm. when small, 10 mm. before opening; color, brown-red.

*Sepals.*—5 sepals, hairy. Color: Brown-red.

*Calyx.*—Funnel-shaped and symsepalous.

*Aspect.*—Spear-shaped.

*Peduncle.*—Brown-red, strong, upright, 4 mm.

Individual flowers:

*Size.*—40–48 mm. and cup-shaped, becoming flat when fully opened.

Color.—Upperside: blue violet to spectrum violet 735. Underside: aster violet 38.

*Borne.*—Every flower stem has 10–14 flowers on short peduncles.

*Shape.*—Five petals; two small and three larger.

*Corolla.*—Each large petal is 24 mm. long and 18–20 mm. wide; the 2 smaller petals are 17 mm. long and 14 mm. wide.

*Arrangement.*—Strong upright peduncles, multiflorous with 10–14 flowers.

Flowering time: Approximately 6 to 7 weeks after potting, the first flowers appear, after which it takes approximately 3 additional weeks to bring the plant to full maturity.

Reproductive organs:

*Anthers.*—Two, 2 mm. × 3 mm., golden yellow; ovary, pilous, seed capsule does not push through.

*Arrangement.*—Basifixed.

*Filaments.*—4 mm. long, color anconite violet 937/1.

*Styles.*—One, color moorish blue 739/3.

*Pollen color.*—Light yellow.

Roots: Normal, well developed root system.

Disease resistance: The resistance of the new cultivar is excellent against botrytis and mildew.

General observations: The new cultivar is characterized as to novelty by its large, solid flower head with large, dark violet blue flowers. Six to eight strong stems 6–8 cm. long support 9–14 flowers above a wreath of fresh green leaves on each plant surrounding the flowers. If started from leaf cutting under good commercial conditions and the same treatment, the plants will flower at the same time. The flowers do not drop from the stem after withering, thereby avoiding damage and destruction due to mildew and botrytis from fallen blossoms.

I claim:

1. A new and distinct cultivar of African Violet plant referred to by the cultivar name Evelyn and particularly characterized as to uniqueness by the combined characteristics of violet-blue flower color, relatively large flower size on strong stems, profuse flowering and long blooming period, foliage color, and fast and vigorous growth.

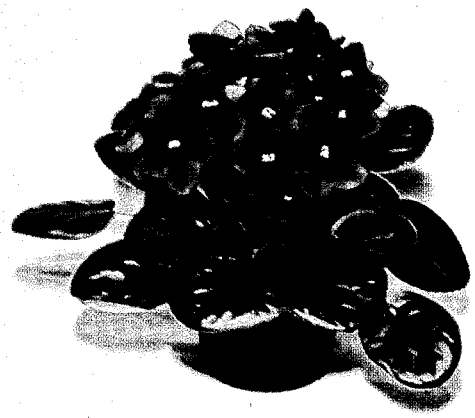

* * * * *